US008921604B2

(12) United States Patent
Becker et al.

(10) Patent No.: US 8,921,604 B2
(45) Date of Patent: Dec. 30, 2014

(54) PROCESS FOR PRODUCING CYCLOHEXYLBENZENE

(75) Inventors: Christopher L. Becker, Manhattan, KS (US); James R. Lattner, LaPorte, TX (US); Charles Morris Smith, Houston, TX (US); Kun Wang, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/983,785

(22) PCT Filed: Nov. 21, 2011

(86) PCT No.: PCT/US2011/061693
§ 371 (c)(1),
(2), (4) Date: Nov. 21, 2013

(87) PCT Pub. No.: WO2012/112203
PCT Pub. Date: Aug. 23, 2012

(65) Prior Publication Data
US 2014/0323766 A1  Oct. 30, 2014

Related U.S. Application Data

(60) Provisional application No. 61/444,338, filed on Feb. 18, 2011.

(30) Foreign Application Priority Data

Apr. 7, 2011 (EP) ..................... 11161515

(51) Int. Cl.
*C07C 45/53* (2006.01)
*C07C 37/08* (2006.01)
*C07C 2/74* (2006.01)

(52) U.S. Cl.
CPC ....................... *C07C 2/74* (2013.01)
USPC ............ 568/342; 568/798; 585/446; 585/467

(58) Field of Classification Search
CPC ............ C07C 45/53; C07C 37/08; C07C 2/74
USPC ............. 568/342, 798; 585/446, 467
See application file for complete search history.

(56) References Cited

U.S. PATENT DOCUMENTS

| 4,094,918 A | 6/1978 | Murtha et al. |
| 4,122,125 A | 10/1978 | Murtha et al. |
| 4,177,165 A | 12/1979 | Murtha et al. |
| 4,206,082 A | 6/1980 | Murtha et al. |
| 4,439,409 A | 3/1984 | Puppe et al. |
| 4,826,667 A | 5/1989 | Zones et al. |
| 4,954,325 A | 9/1990 | Rubin et al. |
| 5,053,571 A | 10/1991 | Makkee |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,049,018 A | 4/2000 | Calabro et al. |
| 6,077,498 A | 6/2000 | Diaz Cabañas et al. |
| 6,201,157 B1 | 3/2001 | Keenan |
| 6,489,529 B1 | 12/2002 | Cheng et al. |
| 6,720,462 B2 | 4/2004 | Kuhnle et al. |
| 6,756,030 B1 | 6/2004 | Rohde et al. |
| 7,579,511 B1 * | 8/2009 | Dakka et al. ............ 585/316 |
| 2008/0242905 A1 * | 10/2008 | Clark et al. ............ 585/323 |

FOREIGN PATENT DOCUMENTS

| EP | 0 293 032 | 11/1988 |
| WO | WO 97/17290 | 5/1997 |
| WO | WO 2009/021604 | 2/2009 |
| WO | WO 2009/025939 | 2/2009 |
| WO | WO 2010/042142 | 4/2010 |
| WO | WO 2010/138248 | 12/2010 |
| WO | WO 2011/001244 | 1/2011 |
| WO | WO 2011/115704 | 9/2011 |

OTHER PUBLICATIONS

Periodic Table of Elements, Chemical Engineering News, vol. 63, No. 5, p. 27 (1985).

* cited by examiner

*Primary Examiner* — Sikarl Witherspoon
(74) *Attorney, Agent, or Firm* — Siwen Chen; Jamie L. Sullivan (57) ABSTRACT

In a process for producing cyclohexylbenzene, benzene is reacted with cyclohexene in a first reaction zone under conditions effective to produce a reaction product comprising cyclohexylbenzene and at least one polycyclohexylbenzene. At least a portion of the reaction product and a stripping agent comprising at least one $C_1$ to $C_{11}$ hydrocarbon or hydrogen are then separately supplied to a separation device and separated into at least a first fraction rich in cyclohexylbenzene and a second fraction rich in the at least one polycyclohexylbenzene.

25 Claims, 2 Drawing Sheets

Fig. 1
(Conventional)

Fig. 2

PROCESS FOR PRODUCING CYCLOHEXYLBENZENE

PRIORITY CLAIM

This application is a National Stage Application of International Application No. PCT/US2011/061693 filed Nov. 21, 2011, which claims priority to U.S. Provisional Application Ser. No. 61/444,338 filed Feb. 18, 2011, and European Application No. 11161515.9 filed Apr. 7, 2011, the disclosures of which are fully incorporated herein by their reference.

FIELD

The present invention relates to a process for producing cyclohexylbenzene.

BACKGROUND

Cyclohexylbenzene is a product of increasing importance in the chemical industry since it offers an alternative route to the Hock process for the production of phenol. The Hock process is a three-step process in which benzene is alkylated with propylene to produce cumene, the cumene is oxidized to the corresponding hydroperoxide and then the hydroperoxide is cleaved to produce equimolar amounts of phenol and acetone.

Oxidation of cyclohexylbenzene has potential as an alternative route for the production of phenol since it co-produces cyclohexanone, which has a growing market and is used as an industrial solvent, as an activator in oxidation reactions and in the production of adipic acid and cyclohexanone resins. However, this alternative route requires the development of a commercially viable process for producing the cyclohexylbenzene precursor.

It has been known for many years that cyclohexylbenzene can be produced from benzene either directly by alkylation with cyclohexene or by the process of hydroalkylation or reductive alkylation. In the latter process, benzene is heated with hydrogen in the presence of a catalyst such that the benzene undergoes partial hydrogenation to produce cyclohexene which then alkylates the benzene starting material. Thus, U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low particularly at economically viable benzene conversion rates and large quantities of unwanted by-products were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting is conducted at a temperature of about 50 to 350° C., a pressure of about 100 to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the hydroperoxide decomposed to the desired phenol and cyclohexanone.

However, although the use of MCM-22 family catalysts has significantly increased product selectivity, the manufacture of cyclohexylbenzene both by direct alkylation and by benzene hydroalkylation still tends to be accompanied by the co-production of significant quantities of by-products. One of the more prevalent contaminants is polycyclohexylbenzenes, which typically comprise up to 20 wt % of the conversion products. Thus, for the overall process to be economically feasible, it is necessary to convert these polycyclohexylbenzenes into additional useful monocyclohexylbenzene product.

One possible method of converting polycyclohexylbenzenes into additional monocyclohexylbenzene is by transalkylation with additional benzene, a solution which is addressed in the '513 patent by effecting the transalkylation in the presence of a catalyst containing the same molecular sieve as used in the hydroalkylation catalyst, namely an MCM-22 family catalyst, but in the absence of the metal components on the hydroalkylation catalyst and in the absence of a hydrogen co-feed. Other transalkylation processes are described in U.S. Pat. No. 6,489,529 and our co-pending PCT Application Nos. PCT/EP2008/006072 and PCT/US2010/031029.

Another process for producing additional cyclohexylbenzene from by-product polycyclohexylbenzenes is described in our co-pending PCT Application No. PCT/2011/023537 and comprises dealkylation of the polycyclohexylbenzenes in the presence of an acid catalyst, such as at least one aluminosilicate, aluminophosphate, or silicoaluminphosphate.

The above methods of converting polycyclohexylbenzenes into additional useful monocyclohexylbenzene product require initial separation of the polycyclohexylbenzenes from the remainder of the alkylation or hydroalkylation process effluent. This is generally effected by a multi-stage fractionation process, in which unreacted benzene and cyclohexylbenzene product are removed from the process effluent in sequential fractionation stages leaving a $C_{12}+$ fraction containing the polycyclohexylbenzenes. Optionally, the $C_{12}+$ fraction is further fractionated to purge a heavies stream from the polycyclohexylbenzenes. Currently, in order to achieve satisfactory separation, each fractionation stage must be operated under vacuum and at a relatively high temperature. Not only is such operation expensive but, in a commercial setting, vacuum operation is likely to result in air ingress and hence formation of oxygenated hydrocarbons. Not only does this lead to loss of valuable product but also the oxygenated hydrocarbons may deactivate the catalyst employed in the downstream transalkylation or dealkylation of the polycyclohexylbenzenes.

According to the invention, it has now been found that separation of cyclohexylbenzene from polycyclohexylbenzenes in the effluent from the reaction of benzene with cyclohexene can be facilitated by the injection of one or more $C_1$ to $C_{11}$ hydrocarbons or hydrogen, or $C_4$ to $C_6$ hydrocarbons, such as in vapor phase, into the separation device (e.g., fractionation unit). This step allows the fractionation unit to be operated at or near atmospheric pressure and a moderate bottoms temperature, typically from about 190° C. to about 300° C., especially from about 190° C. to about 241° C.

SUMMARY

In one aspect, the invention resides in a process for producing cyclohexylbenzene, the process comprising:

(a) reacting benzene with cyclohexene under conditions effective to produce cyclohexylbenzene and at least one polycyclohexylbenzene;

(b) supplying a feed comprising at least a portion of the cyclohexylbenzene and at least a portion of the at least one polycyclohexylbenzene to a separation device to separate the feed into at least a first fraction rich in cyclohexylbenzene and a second fraction rich in the at least one polycyclohexylbenzene; and (c) separately supplying a stripping agent comprising at least one $C_1$ to $C_{11}$ hydrocarbon or hydrogen to the separation device at a location below where the feed in (b) is supplied to the separation device.

Conveniently, the stripping agent is a $C_4$ to $C_6$ hydrocarbon, such as benzene.

Conveniently, the stripping agent is a vapor.

Conveniently, the stripping agent is supplied to the separation device in (c) is at a temperature of about 190° C. to about 241° C.

Conveniently, the ratio of the weight of the stripping agent supplied to the separation device in (c) to the weight of the reaction product supplied to the separation device in (b) is from about 0.05:1 to about 2:1, such as from about 0.1:1 to about 1:1, for example about 0.5:1.

Conveniently, the separation device comprises a fractionation column and the stripping agent is supplied at or adjacent the base of the fractionation column.

In one embodiment, the stripping agent comprises benzene. Conveniently, at least part of the benzene vapor supplied to the separation device in (c) is obtained from unreacted benzene present in the reaction product produced in (a).

In one embodiment, the cyclohexene employed in (a) is produced by hydrogenation of benzene in situ in the reaction zone. Conveniently, the hydrogenation of benzene and the reacting (a) are conducted in the presence of a catalyst comprising a metal-containing zeolite of the MCM-22 family.

In a further aspect, the invention resides in a process for producing cyclohexylbenzene, the process comprising:

(a) hydroalkylating benzene with hydrogen in a first reaction zone under conditions effective to produce unreacted benzene, cyclohexylbenzene and at least one polycyclohexylbenzene;

(b) separately supplying (i) a feed comprising at least a portion of the unreacted benzene, the cyclohexylbenzene and at least a portion of the at least one polycyclohexylbenzene; and (ii) a stripping agent comprising at least one $C_1$ to $C_{11}$ hydrocarbon or hydrogen to a separation device to separate into at least a first fraction rich in cyclohexylbenzene and a second fraction rich in the at least one polycyclohexylbenzene, wherein the stripping agent is provided to the separation device at a location below where the feed is supplied to the separation device; and (c) transalkylating at least a portion of the at least one polycyclohexylbenzene from the second fraction in the presence of benzene to produce a product comprising additional cyclohexylbenzene.

DETAILED DESCRIPTION OF THE EMBODIMENTS

Described herein is a process for producing cyclohexylbenzene by reacting benzene with cyclohexene to produce cyclohexylbenzene and at least one polycyclohexylbenzene. The cyclohexylbenzene and at least one polycyclohexylbenzene are then fed to a separation device along with a stripping agent comprising at least one $C_1$ to $C_{11}$ hydrocarbon or hydrogen, such as a $C_4$ to $C_6$ hydrocarbon, preferably in the vapor phase, so as to facilitate separation of the feed into at least a first fraction rich in cyclohexylbenzene and a second fraction rich in at least one polycyclohexylbenzene. As will be discussed in more detail below, the cyclohexylbenzene is recovered from the first fraction and then generally converted to phenol and cyclohexanone whereas the at least one polycyclohexylbenzene in the second fraction is either dealkylated or transalkylated with benzene to generate additional cyclohexylbenzene.

Production of the Cyclohexylbenzene

In the initial step in the present process, cyclohexylbenzene is produced by contacting benzene with cyclohexene in the presence of a catalyst having an alkylation function and under conditions to promote the following reaction:

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

Any commercially available benzene feed can be used in the hydroalkylation, but preferably the benzene has a purity level of at least 99 wt %. Similarly, although the source of hydrogen is not critical, it is generally desirable that the hydrogen is at least 99 wt % pure.

Conveniently, the total feed to the hydroalkylation contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

- molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
- molecular sieves made from a common second degree building block, being a 2-dimensional tiling of such MWW framework topology unit cells, forming a monolayer of one unit cell thickness, preferably one c-unit cell thickness;
- molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
- molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

In one embodiment, the hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials, such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Treatment of the Cyclohexylbenzene Product

Although the hydroalkylation reaction using an MCM-22 family zeolite catalyst is highly selective towards cyclohexylbenzene, the liquid effluent from the hydroalkylation reaction will inevitably contain significant quantities of unreacted benzene and certain by-products in addition to the desired cyclohexylbenzene. One of the major by-products is polycyclohexylbenzene (di- and/or tricyclohexylbenzene), which typically comprise up to 20 wt % of the conversion products. In various embodiments, the effluent from the hydroalkylation reaction contains at least 1 wt %, or at least 5 wt %, or at least 10 wt % of the polycyclohexylbenzene, based upon total weight of the effluent. It is typically desirable to convert these polycyclohexylbenzenes into additional useful cyclohexylbenzene product. This can be achieved by transalkylation or dealkylation, but initially it is desirable to separate the polycyclohexylbenzenes from the desired product.

In the present process, separation of the polycyclohexylbenzenes is achieved by supplying at least a portion of a feed comprising cyclohexylbenzene, one or more polycyclohexylbenzenes and, optionally, unreacted benzene (e.g., from the hydroalkylation reaction) to a separation device (e.g., fractionation device), normally a fractionation column, to separate the feed into at least a first fraction rich in cyclohexylbenzene and a second fraction rich in the one or more polycyclohexylbenzenes. When a fraction is described as being "rich in" in a specified species, it is meant that the wt % of the specified species in that fraction is enriched relative to the feed stream (i.e., the input).

In one embodiment, to allow the separation to be effected at or near atmospheric pressure (about 100 kPa to about 300 kPa) and at relatively low temperatures, a stripping agent comprising at least one $C_1$ to $C_{11}$ hydrocarbon or hydrogen is supplied separately to the separation device. In various embodiments, the stripping agent is a $C_4$ to $C_6$ hydrocarbon, such as benzene. In various embodiments, the stripping agent is supplied in the vapor phase Conveniently, the stripping agent is supplied to the separation device in (c) at a temperature of about 190° C. to about 300° C. More particularly, where steam is used to heat and vaporize the stripping agent, the temperature of the stripping agent vapor supplied to the separation device in (c) is between about 190° C. and about 241° C.

In another embodiment, the stripping agent is supplied in the liquid phase to the separation device and heated in situ to the vapor or partial vapor phase. Generally, the ratio of the weight of the stripping agent vapor supplied to the separation device to the weight of feed supplied to the separation device is from about 0.05:1 to about 2:1, such as from about 0.1:1 to about 1:1, for example about 0.5:1.

In one embodiment, the stripping agent is supplied at a location below where the feed comprising cyclohexylbenzene, one or more polycyclohexylbenzenes and, optionally, unreacted benzene is supplied to the separation device. In one embodiment, stripping agent hydrocarbon is supplied to the bottom half of the separation device. In one embodiment, the stripping agent is supplied at or adjacent the base of the fractionation column. Although any stripping agent hydrocarbon vapor can be used, benzene vapor is particularly useful since, for example, the hydroalkylation reaction effluent contains significant quantities (typically up to 60 wt %) of unreacted benzene.

In one embodiment of the present process, after separation from the hydroalkylation reaction effluent, the polycyclohexylbenzenes are mixed with benzene and transalkylated to produce additional monocyclohexylbenzene. Transalkylation is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,049,018), zeolite Y and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

In another embodiment of the present process, conversion of the polycyclohexylbenzenes to additional monocyclohexylbenzene is effected by dealkylation. Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate. Dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10. Various dealkylation processes are described in more detail in co-pending Application No. PCT/2010/031029.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexane (BCH) and methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation and so, if not removed, will build up in the $C_{1-2}$ stream. Similarly, bicyclohexane (BCH) can lead to separation problems downstream.

bicyclohexane 1,2-methylcyclopentylbenzene 1,3-methylcyclopentylbenzene 1,1-methylcyclopentylbenzene Thus, at least part of the hydroalkylation reaction product may be treated with a catalyst under conditions to remove at least 1,1-methylcyclopentylbenzene and/or bicyclohexane from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexane is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene-rich stream separated from the hydroalkylation reaction product is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2dicarboximide, N -hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to a cleavage reaction. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to a cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to a cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include Brønsted acids and Lewis acids, such as, but are not limited to, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight -parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical induced conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Suitable cleavage conditions include a temperature of at least 20° C. and no greater than 200° C., or at least 40° C. and no greater than 120° C., and a pressure of at least 1 psig and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the heat generated from the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, each of which may generally comprise about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product may be neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay, such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis, such as sodium acetate, sodium bicarbonate, sodium phenate, and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines, and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa, gauge to 3450 kPa, gauge), or about 10 psig to 200 psig (70 kPa to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which can be purified and separated by methods well known in the art.

Figure 1:
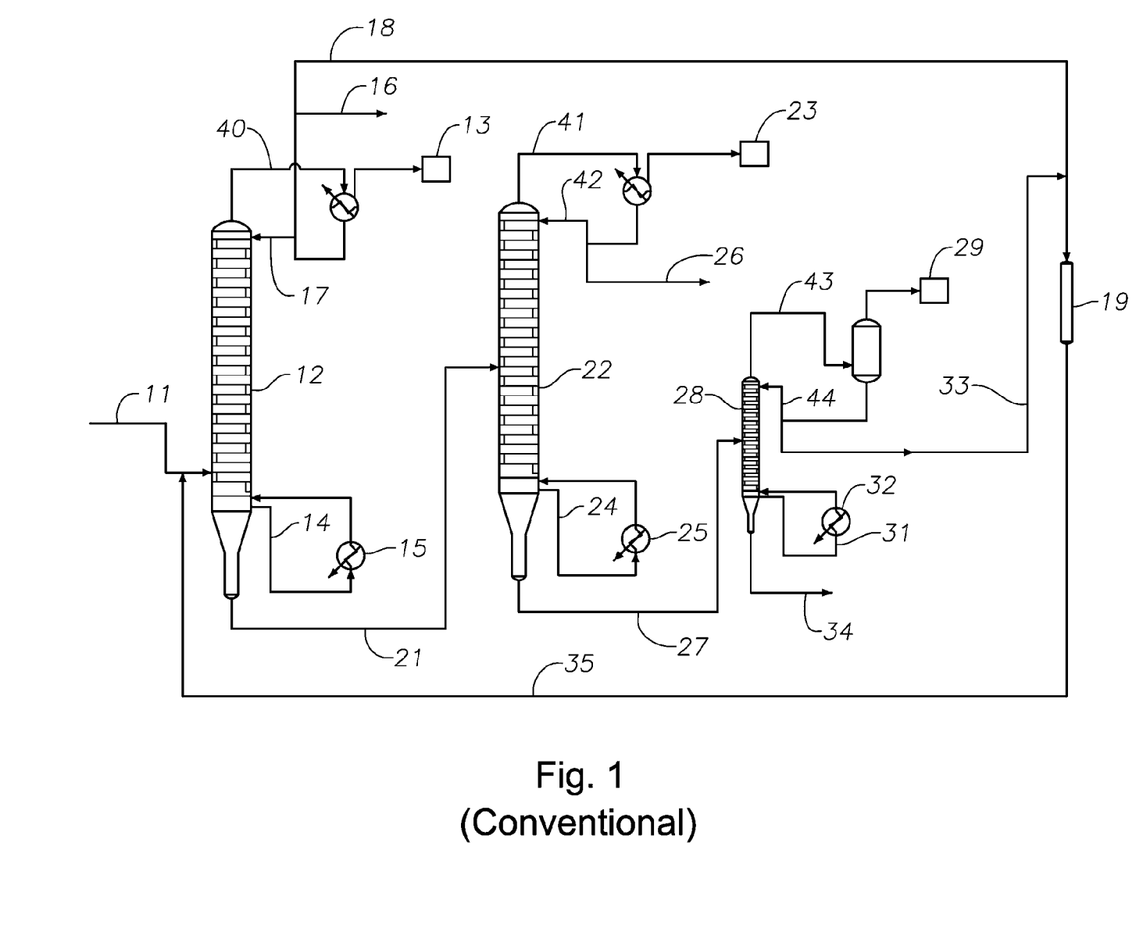
FIG. 1 is a flow diagram of a conventional process for treating the product of a benzene hydroalkylation reaction.
Figure 2:
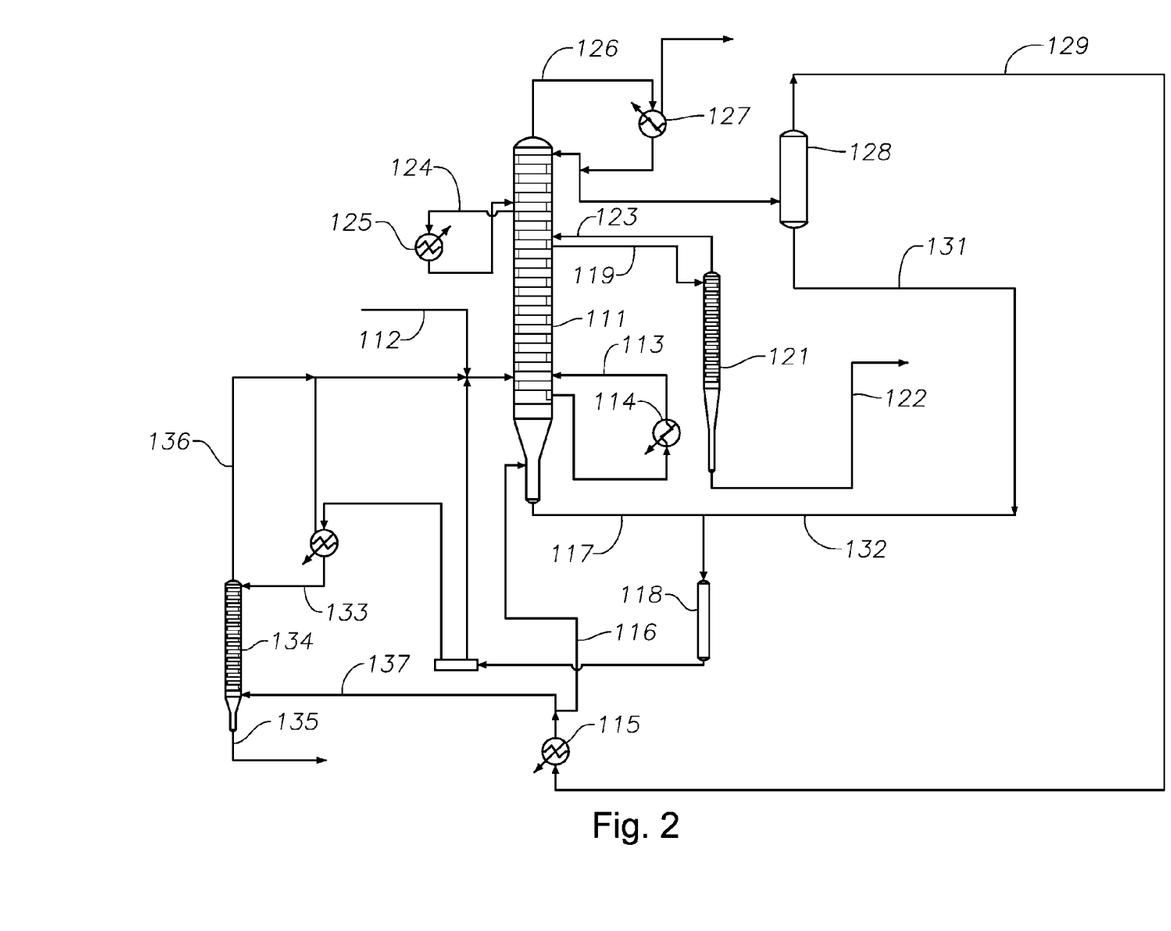
FIG. 2 is a flow diagram of a process according to a first example of the invention for treating the product of a benzene hydroalkylation reaction.

The invention will now be more particularly described with reference to the accompanying drawings, in which FIG. 1 is a flow diagram of a conventional process for treating the product of a benzene hydroalkylation reaction, whereas FIG. 2 is a flow diagram of a process for treating such a product according to a first example of the present invention.

Referring to FIG. 1, in the conventional process, the product from a benzene hydroalkylation reaction, comprising cyclohexylbenzene, one or more polycyclohexylbenzenes and unreacted benzene, is fed through line 11 to a first fractionation column 12. The reaction product is typically at a temperature of about 120° C. to about 140° C. as it enters the column 12 and is supplied to the column close the base of the column. At its upper end the column 12 is connected to a vacuum source 13 such that the column 12 is typically operated at a pressure of about 20 kPa to about 50 kPa. Adjacent the base of the column 12, a slipstream 14 may be removed from the column, passed through a heater 15 and recycled to the column such that the temperature at the base of the column 12 is typically between about 200° C. and about 241° C.

The benzene hydroalkylation reaction product is fractionated in the column 12 to produce a C$_6$ fraction rich in unreacted benzene and a C$_{12}$+ fraction rich in cyclohexylbenzene, polycyclohexylbenzenes and other heavies. The C$_6$ fraction is removed from the upper end the column 12 via line 40 with the assistance of the vacuum source 13 and may be recycled in whole or in part to the benzene hydroalkylation reactor (not shown) via line 16. A portion of the stream in line 40 may be recycled in part to the column 12 as a reflux stream 17, and may be fed in part via line 18 to a transalkylation reactor 19. The $C_{12}+$ fraction is removed from the column 12 via line 21 and is supplied to a second fractionation column 22.

The upper end of the second column 22 is connected to a vacuum source 23 such that the column 22 is typically operated at a pressure of about 10 kPa to about 20 kPa. In addition, a slipstream 24 may be removed from near the base of the column 22 and may be passed through a heater 25 before being recycled to the column 22 such that the temperature at the base of the column 22 is typically between about 220° C. and about 241° C. The $C_{12}+$ fraction is divided in the column 22 into an overhead fraction rich in cyclohexylbenzene via line 41 and a bottoms fraction rich in polycyclohexylbenzenes via line 27. A portion of the overhead fraction in line 41 is removed via line 26 for further processing of the cyclohexylbenzene, whereas the bottoms fraction is supplied via line 27 to a third fractionation column 28. A portion of the stream in line 41 may be recycled to column 22 as reflux stream 42.

The third column 28 is connected at its upper end to a high vacuum source 29 such that the column 28 is typically operated at a pressure of about 1 kPa to about 10 kPa. Further, a slipstream 31 is removed from near the base of the column 28 and passed through a heater 32 before being recycled to the column 28 such that the temperature at the base of the column 28 is typically between about 220° C. and about 241° C. The column 28 fractionates the overhead fraction via line 43 from the column 22 into a first fraction rich in polycyclohexylbenzenes which is supplied via line 33 to the transalkylation reactor 19 and a heavies fraction which is removed via line 34 for purging or for use as a fuel. A portion of the stream in line 43 may be recycled to column 28 as reflux stream 44.

The polycyclohexylbenzenes in line 33 are reacted with the benzene from line 18 in the transalkylation reactor 19 to produce a transalkylation reaction effluent, which comprises mainly cyclohexylbenzene and unreacted benzene and which is fed via line 35 back to the first fractionation column 12.

Referring now to FIG. 2, in a process according to the present invention, the hydroalkylation reaction product is again fed to a first fractionation column 111, in this case via the line indicated at 112. Again a slipstream 113 may be removed from adjacent the base of the column 111, passed through a heater 114 and recycled to the column. In addition, however, benzene recovered from the overhead from the column 111 via line 129 is preheated and vaporized in a further heater 115 and is injected by way of line 116 into the base of the column 111. In this way, using pressurized steam to heat the recycled benzene, the temperature at the base of the column 111 can be readily maintained between about 190° C. and about 241° C. At this temperature, even with the column 111 being operated at or above atmospheric pressure (100 kPa to 300 kPa), substantially all of the $C_{12}$ and lower hydrocarbon components are in the vapor phase at the base of the column 111. Thus the liquid bottoms stream leaving the column 111 is composed mainly of polycyclohexylbenzenes and other heavy products and can be fed via line 117 directly to a transalkylation reactor 118.

At or slightly above the mid-point of the column 111, a liquid side stream may be removed from the column 111 and fed by way of line 119 to a second fractionation column 121. Since the side stream is substantially free of $C_{18}+$ hydrocarbons, the column 121 can be operated above atmospheric pressure (typically at 105 kPa to 110 kPa) to separate the side stream into cyclohexylbenzene-rich bottoms stream and a benzene-rich overhead stream. The cyclohexylbenzene-rich bottoms stream may be recovered via line 122 for further processing whereas the benzene-rich overhead stream may be returned to the column 111 via line 123.

To assist in separation of benzene and cyclohexylbenzene in the column 111, a slip stream may be removed from the column 111, for example, above the location of the line 123 via line 124 and passed through a cooler 125 before being returned to the column 111. In this way, the vapor phase overhead leaving the column via line 126 is composed substantially entirely of benzene and light ($C_6=$) impurities. The overhead is initially passed through a condenser 127 where the light impurities are removed for use as fuel and the benzene is condensed before being passed to a vaporization unit 128. The benzene may be heated and revaporized in the unit 128 and the resultant benzene vapor is fed at least partially via line 129 to the heater 115, partly via line 131 to the hydroalkylation unit (not shown) and partly via line 132 to the transalkylation reactor 118.

The benzene vapor from line 132 and the polycyclohexylbenzenes (both di- and tricyclohexylbenzene) in the column 111 bottoms react in the transalkylation reactor 118 to produce additional cyclohexylbenzene. The effluent from the transalkylation reactor 118 may be fed by line 133 to a third fractionation column 134, where unreacted heavy (C24+) hydrocarbons are removed for purging via bottoms line 135 and a vapor phase rich in cyclohexylbenzene is removed via overhead line 136 and fed to the first fractionation column 111. To allow operation of the third fractionation column 134 at atmospheric pressure and low bottoms temperatures (typically about 220° C. to about 241° C.), part of the heated benzene vapor from the heater 115 may be supplied to the base of the column 134 via line 137.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising:
   (a) reacting benzene with cyclohexene under conditions effective to produce cyclohexylbenzene and at least one polycyclohexylbenzene;
   (b) supplying a feed comprising at least a portion of the cyclohexylbenzene and at least a portion of the at least one polycyclohexylbenzene to a separation device to separate the feed into at least a first fraction rich in cyclohexylbenzene and a second fraction rich in the at least one polycyclohexylbenzene; and
   (c) separately supplying a stripping agent comprising at least one $C_1$ to $C_{11}$ hydrocarbon or hydrogen to the separation device at a location below where the feed in (b) is supplied to the separation device.

2. The process of claim 1, wherein the stripping agent comprises at least one $C_4$ to $C_6$ hydrocarbon.

3. The process of claim 1, wherein the stripping agent is benzene.

4. The process of claim 1, wherein at least a portion of the stripping agent is heated to the vapor phase in the separation device.

5. The process of claim 1, wherein at least a portion of the stripping agent is supplied to the separation device in the vapor phase.

6. The process of claim 1, wherein the stripping agent supplied to the separation device in (c) is at a temperature of about 190° C. to about 300° C.

7. The process of claim 1, wherein the ratio of the weight of the stripping agent supplied to the separation device in (c) to the weight of the feed supplied to the separation device in (b) is from about 0.05:1 to about 2:1.

8. The process of claim 1, wherein the ratio of the weight of the stripping agent supplied to the separation device in (c) to the weight of the reaction product supplied to the separation device in (b) is about 0.5:1.

9. The process of claim 1, wherein the separation device comprises a fractionation column.

10. The process of claim 9, wherein the fractionation column is operated at a pressure of about 100 kPa to about 300 kPa.

11. The process of claim 9, wherein the stripping agent is supplied at or adjacent the base of the fractionation column.

12. The process of claim 1, wherein step (a) further produces unreacted benzene, and the unreacted benzene is supplied to the separation device in (c) as the stripping agent.

13. The process of claim 1, and further comprising:
(d) transalkylating at least a portion of the at least one polycyclohexylbenzene from the second fraction in the presence of benzene to produce a product comprising additional cyclohexylbenzene.

14. The process of claim 13, wherein at least part of the product from (d) is supplied to the separation device in (b).

15. The process of claim 1, wherein the polycyclohexylbenzene comprises at least one of dicyclohexylbenzene and tricyclohexylbenzene.

16. The process of claim 1, wherein the cyclohexene is generated by hydrogenation of benzene in situ in (a).

17. The process of claim 16, wherein the hydrogenation of benzene and the reacting (a) are conducted in the presence of a catalyst comprising a metal-containing zeolite of the MCM-22 family.

18. The process of claim 1, wherein step (a) further produces unreacted benzene, and the unreacted benzene is recycled back as the benzene used in step (a).

19. A process for producing cyclohexylbenzene, the process comprising:
(a) hydroalkylating benzene with hydrogen in a first reaction zone under conditions effective to produce unreacted benzene, cyclohexylbenzene and at least one polycyclohexylbenzene;
(b) separately supplying: (i) a feed comprising at least a portion of the unreacted benzene, the cyclohexylbenzene and at least a portion of the at least one polycyclohexylbenzene;
and (ii) a stripping agent comprising at least one $C_1$ to $C_{11}$ hydrocarbon or hydrogen to a separation device and separated into at least a first fraction rich in cyclohexylbenzene and a second fraction rich in the at least one polycyclohexylbenzene, wherein the stripping agent is provided to the separation device at a location below where the feed in (i) is supplied to the separation device; and
(c) transalkylating at least a portion of the at least one polycyclohexylbenzene from the second fraction in the presence of benzene to produce a product comprising additional cyclohexylbenzene.

20. The process of claim 19, wherein the stripping agent comprises at least one $C_4$ to $C_6$ hydrocarbon.

21. The process of claim 19, wherein the stripping agent is benzene.

22. The process of claim 19, wherein the stripping agent is supplied to the separation device in (b) at a temperature of about 190° C. to about 300° C.

23. The process of claim 19, wherein the separation device comprises a fractionation column.

24. The process of claim 23, wherein the fractionation column is operated at a pressure of about 100 kPa to about 300 kPa.

25. The process of claim 19, and further comprising:
(d) oxidizing the cyclohexylbenzene from the first fraction from (b) and the product from (c) to produce a cyclohexylbenzene hydroperoxide; and
(e) cleaving the cyclohexylbenzene hydroperoxide from the oxidizing (d) to produce phenol and cyclohexanone.

* * * * *